United States Patent
Whitmore et al.

(10) Patent No.: US 6,417,425 B1
(45) Date of Patent: Jul. 9, 2002

(54) ABSORBENT ARTICLE AND PROCESS FOR PREPARING AN ABSORBENT ARTICLE

(75) Inventors: Darryl L. Whitmore, Chesapeake, VA (US); Fritz Engelhardt, Frankfurt (DE)

(73) Assignee: BASF Corporation, Mount Olive, NJ (US)

( * ) Notice: Subject to any disclaimer, the term of this patent is extended or adjusted under 35 U.S.C. 154(b) by 0 days.

(21) Appl. No.: 09/495,209

(22) Filed: Feb. 1, 2000

(51) Int. Cl.$^7$ .................................................. A61F 13/15
(52) U.S. Cl. ..................... 604/367; 427/389.9; 427/391; 604/368; 604/366
(58) Field of Search .................................. 604/365, 367, 604/368, 374, 375, 376; 427/372.2, 385.5, 389.8, 389.9, 391, 392, 393.5; 428/376; 442/417

(56) References Cited

U.S. PATENT DOCUMENTS

| | | | |
|---|---|---|---|
| 3,229,769 A | * 1/1966 | Bashaw et al. ................. 169/1 |
| 3,707,148 A | 12/1972 | Bryce |
| 3,794,034 A | 2/1974 | Jones |
| 3,964,486 A | 6/1976 | Blaney |
| 4,076,663 A | 2/1978 | Masuda |
| 4,102,340 A | 7/1978 | Mesek |
| 4,192,727 A | * 3/1980 | Ward ......................... 204/159 |
| 4,269,188 A | 5/1981 | Nishizawa |
| 4,286,082 A | 8/1981 | Tsubakimoto |
| 4,340,706 A | 7/1982 | Obayashi |
| 4,354,487 A | 10/1982 | Oczkowski |
| 4,381,320 A | 4/1983 | Nguyen |
| 4,382,919 A | 5/1983 | Alonso |
| 4,443,492 A | 4/1984 | Roller |
| 4,497,930 A | 2/1985 | Yamasaki |
| 4,500,315 A | 2/1985 | Pieniak |
| 4,507,438 A | 3/1985 | Obasyashi |
| 4,537,590 A | 8/1985 | Pieniak |
| 4,540,454 A | 9/1985 | Pieniak |
| 4,559,050 A | 12/1985 | Iskra |
| 4,560,372 A | 12/1985 | Pieniak |
| 4,573,988 A | 3/1986 | Pieniak |
| 4,596,567 A | 6/1986 | Iskra |
| 4,605,402 A | 8/1986 | Iskra |
| 4,657,537 A | 4/1987 | Zimmerer |
| 4,666,975 A | 5/1987 | Yamasaki |
| 4,676,784 A | 6/1987 | Erdman |
| 4,683,274 A | 7/1987 | Nakamura |
| 4,734,478 A | 3/1988 | Tsubakimoto |
| 4,748,076 A | 5/1988 | Saotome |
| 4,762,521 A | 8/1988 | Roessler |
| 4,770,656 A | 9/1988 | Proxmire |
| 4,798,603 A | 1/1989 | Meyer |
| 4,944,735 A | 7/1990 | Mokry |
| 5,071,681 A | * 12/1991 | Manning et al. ............. 427/392 |
| 5,079,034 A | * 1/1992 | Miyake et al. ............. 427/45.1 |
| 5,100,397 A | 3/1992 | Poccia |
| 5,145,906 A | 9/1992 | Chambers |
| 5,171,237 A | 12/1992 | Poccia |
| 5,246,429 A | 9/1993 | Poccia |
| 5,352,480 A | 10/1994 | Hansen |
| 5,364,382 A | 11/1994 | Latimer |
| 5,498,478 A | * 3/1996 | Hansen et al. ............... 428/372 |
| 5,567,478 A | 10/1996 | Houben |
| 5,607,550 A | * 3/1997 | Akers ......................... 162/102 |
| 5,662,633 A | 9/1997 | Doak |
| 5,853,867 A | * 12/1998 | Harada et al. ............ 428/317.9 |
| 5,868,724 A | 2/1999 | Dierckes |
| 5,955,187 A | * 9/1999 | McCormack et al. ........ 428/315 |
| 6,043,311 A | 3/2000 | Houben |
| 6,071,549 A | * 6/2000 | Hansen ....................... 427/2.31 |
| 6,251,479 B1 | * 6/2001 | Groitzsch et al. ........... 427/244 |
| 6,270,845 B1 | * 8/2001 | Pappas et al. ............ 427/385.5 |
| 6,300,259 B1 | * 10/2001 | Westland et al. ............ 442/153 |

FOREIGN PATENT DOCUMENTS

| | | |
|---|---|---|
| EP | 0 040 087 A2 | 11/1981 |
| EP | 0 040 087 A3 | 11/1981 |
| EP | 0 290 814 B1 | 11/1988 |
| EP | 0 290 814 A2 | 11/1988 |
| EP | 0 315 185 B1 | 5/1989 |
| EP | 0 402 650 A2 | 12/1990 |
| EP | 0 454 497 A2 | 10/1991 |
| EP | 0 702 031 A2 | 3/1996 |
| EP | 0 708 119 A1 | 4/1996 |
| EP | 0 763 364 A2 | 3/1997 |
| GB | 1034296 | 6/1966 |
| WO | WO 93/18223 | 9/1993 |
| WO | WO 96/23024 | 8/1996 |

OTHER PUBLICATIONS

Mitsubishi Petrochemical Co. Ltd. "Water–absorbing composite materials prodn. used in sanitary towel mfr." published Mar. 9, 1987—Derwent Abstract Did Not Receive.

Mitsubishi Petrochemical Co. Ltd. "Water absorbing composite materials prodn." published Jan. 31, 1987—JP 94089077—Derwent Abstract.

Mitsubishi Petrochemical Co. Ltd. —"Water absorbing composite prodn." published May 15, 1989—JP 95119262—Derwent Abstract.

Mitsubishi Petrochemical Co. Ltd. —"Water absorbing composite, for sanitary materials" published May 15, 1989—JP95119263—Derwent Abstract.

Mitsubishi Petrochemical Co. Ltd. —"Water absorptive composite prod. for sanitary use" published Mar. 30, 1990—JP 95110899—Derwent Abstract.

* cited by examiner

Primary Examiner—John G. Weiss
Assistant Examiner—Jacqueline F Stephens
(74) Attorney, Agent, or Firm—David T. Banchik

(57) ABSTRACT

Absorbent articles and processes for making absorbent articles are provided. The process includes spraying onto a fibrous web a blend containing superabsorbent polymer particles, superabsorbent forming monomer, initiator and water, and subjecting the web to polymerization conditions. The resulting web is useful as an absorbent article particularly in disposable hygiene products.

4 Claims, No Drawings

ABSORBENT ARTICLE AND PROCESS FOR PREPARING AN ABSORBENT ARTICLE

BACKGROUND OF THE INVENTION

The present invention relates to an absorbent article, particularly an absorbent article which is useful in personal care products.

DESCRIPTION OF THE RELATED ART

Personal care products for the absorption of body fluids are known. Such products include adult incontinence products, diapers, training pants, feminine care products, wound dressings and the like. As a general rule, such personal care products generally comprise an amount of a cellulosic fiber such as wood pulp fluff. Wood pulp fluff is known to be a suitable absorbent for body fluids. As a general rule, 1 gram of wood pulp fluff is able to absorb from about 5 to about 8 grams of a discharged body fluid such as urine. A personal care product such as an infant diaper, generally has an absorbent capacity of at least about 200 to 400 grams of urine. Thus, when such an infant diaper is formed from wood pulp fluff, a relatively large quantity of wood pulp fluff must be employed.

In order to reduce the amount of wood pulp fluff and the corresponding bulk of such an infant diaper, it is known to include high absorbency materials known in the art as superabsorbents. Such high absorbency materials are generally capable of absorbing at least about 10, preferably at least about 20, and up to 50 or more times their weight in water. By incorporating such high absorbency materials in infant diapers, it is possible to reduce the overall bulk of the diaper while maintaining its absolute absorbent capacity.

Nonetheless, the use of such high absorbency materials is not without problems. For example, some high absorbency materials are known to cause gel blocking. That is, as the high absorbency materials become swollen with a liquid, they form a gelatinous mass which prevents the free flow of liquid therethrough. Thus, while the high absorbency materials may be able to absorb an initial insult (in other words, exposure to fluid), subsequent insults are unable to pass through the now swollen high absorbency material. As a result, subsequent insults tend to pool and run off of the absorbent product resulting in leakage.

Accordingly, a number of different structures have been proposed to alleviate or reduce the problems associated with incorporating high absorbency materials in personal care products.

U.S. Pat. No. 4,699,619 issued Oct. 13, 1987, to Bernardin describes a multilayer absorbent composite having a first relatively low density layer and a second relatively high density layer underlying at least a portion of the first layer. A high absorbency material (superabsorbent) is described as being located between said first and second layers.

U.S. Pat. No. 4,102,340 issued Jul. 25, 1978, to Mesek et al. is directed to a disposable article with a particulate hydrophilic polymer in an absorbent bed. Described is an absorbent pad comprising a fibrous structure having an intermediate densified layer and a layer of highly porous, loosely compacted ban on both sides of the densified layer. One of the batt layers is described as including a particulate, water-insoluble but water-swellable polymeric absorbent.

U.S. Pat. No. 4,269,188 issued May 26, 1981, to Nishizawa et al. is directed to a disposable diaper. Disclosed is a disposable diaper including an absorbent material comprising a laminate wherein a water-absorbent polymer powder is fixed between two sheets of paper. A fluff pulp layer is located on both sides of the laminate containing a water-absorbing polymer.

While the structures described in the referenced patents have often proven beneficial, they have not completely solved the problems associated with the use of high-absorbency materials. In use, the wood pulp fluff generally serves to quickly absorb a discharged body fluid. The fluid is generally held in the pores of the fluff matrix. The high absorbency material in the fluff matrix then absorbs the fluid and, in effect, dewaters the fluff matrix. That is, the fluff serves to absorb and hold surges (relatively large quantities applied relatively quickly) of body fluid until the high-absorbency material can absorb the body fluid. Moreover, many known personal care products employ high-absorbency materials in relatively low quantities. This is because the cost of such high-absorbency materials is generally greater than the cost of a material such as wood pulp fluff. It is sometimes desirable to employ a relatively high concentration of high-absorbency material when forming a personal care product. As the concentration of high-absorbency material increases in an absorbent product, the concentration of wood pulp fluff generally decreases. The high-absorbency materials are not generally able to absorb urine at the rate at which it is applied. This may lead to leakage in absorbent structures having high concentrations of absorbent materials.

It is desired to provide an absorbent structure which may contain an absorbent layer having a relatively high concentration of high-absorbency material but which absorbent structure is capable of quickly absorbing body fluids applied thereto.

It is further desired to provide an absorbent structure, and a process for preparing such an absorbent structure, wherein superabsorbent materials are affixed to a matrix. It is further desired to provide a matrix wherein superabsorbent polymer is uniformly distributed and which exhibits wet strength integrity. Such a structure reduces the likelihood of superabsorbent shifting and thereby creating regions of high and low concentration of superabsorbent which can result in uneven absorption of fluids.

SUMMARY OF THE INVENTION

The present invention provides a process comprising:
  forming a sprayable blend comprising
    one or more superabsorbent forming monomers
    superabsorbent polymer particles
    water, and
    one or more initiators;
  spraying said sprayable blend onto a fibrous web; and
  subjecting said fibrous web to conditions under which the superabsorbent forming monomer will polymerize.

The present invention further provides a superabsorbent article prepared by the above-described process.

DETAILED DESCRIPTION OF THE INVENTION

The process of the present invention requires the formation of a sprayable blend comprising superabsorbent monomer, superabsorbent polymer particles, water and initiator.

Superabsorbent Forming Monomer

Superabsorbent forming monomer, as used herein, refers to polymerizable compounds which contribute to the absorbency of the polymers formed therefrom. Suitable superabsorbent forming monomers useful in the present invention include monoethylenically unsaturated compounds (or compounds having a polymerizable double bond), having at least one hydrophilic radical, such as carboxyl, carboxylic acid anhydride, carboxylic acid salt, sulfonic acid, sulfonic acid salt, hydroxyl, ether, amide, amino and quaternary ammonium salt groups. Examples of suitable superabsorbent forming monomers are as follows:

1. Carboxyl group-containing monomers: monoethylenically unsaturated mono or poly-carboxylic acids, such as (meth)acrylic acid (meaning acrylic acid or methacrylic acid. Similar notations are used hereinafter), maleic acid, fumaric acid; crotonic acid, sorbic acid, itaconic acid, and cinnamic acid 2. Carboxylic acid anhydride group-containing monomers: monoethylenically unsaturated polycarboxylic acid anhydrides (such as maleic anhydride);

3. Carboxylic acid salt-containing monomers: water-soluble salts (alkali metal salts, ammonium salts, amine salts, etc.) of monoethylenically unsaturated mono- or poly-carboxylic acids [such as sodium (meth)acrylate, trimethylamine (meth)acrylate, triethanolamine (meth)acrylate, sodium maleate, methylamine maleate];

4. Sulfonic acid group-containing monomers: aliphatic or aromatic vinyl sulfonic acids (such as vinylsulfonic acid, allyl sulfonic acid, vinyltoluenesulfonic acid, styrene sulfonic acid), (meth)acrylic sulfonic acids [such as sulfopropyl (meth)acrylate, 2-hydroxy-3-(meth)acryloxy propyl sulfonic acid];

5. Sulfonic acid salt group-containing monomers: alkali metal salts, ammonium salts, amine salts of sulfonic acid group-containing monomers as mentioned above.

6. Hydroxyl group-containing monomers: monoethylenically unsaturated alcohols [such as (meth)allyl alcohol], monoethylenically unsaturated ethers or esters of polyols (alkylene glycols, glycerol, polyoxyalkylene polyols), such as hydroxethyl (meth)acrylate, hydroxypropyl (meth) acrylate, triethylene glycol (meth)acrylate, poly (oxyethylene oxypropylene) glycol mono (meth)allyl ether (in which hydroxyl groups may be etherified or esterified).

7. Amide group-containing monomers: vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N,N'-di-n-propylacrylamide), N-hydroxyalkyl (meth)acrylamides [such as N-methylol(meth)acrylamide, N-hydroxyethyl (meth)acrylamide], N,N-dihydroxyalkyl (meth)acrylamides [such as N,N-dihydroxyethyl (meth)acrylamide], vinyl lactams (such as N-vinylpyrrolidone);

8. Amino group-containing monomers: amino group-containing esters (e.g. dialkylaminoalkyl esters, dihydroxyalkylaminoalkyl esters, morpholinoalkyl esters, etc.) of monoethylenically unsaturated mono- or di-carboxylic acid [such as dimethlaminoethyl (meth)acrylate, diethylaminoethyl (meth)acrylate, morpholinoethyl (meth)acrylate, dimethyl aminoethyl fumarate], heterocyclic vinyl compounds [such as vinyl pyridines (e.g. 2-vinyl pyridine, 4-vinyl pyridine, N-vinyl pyridine), N-vinyl imidazol]; and 9. Quaternary ammonium salt group-containing monomers: N,N,N-trialkyl-N-(meth)acryloyloxyalkylammonium salts [such as N,N,N-trimethyl-N-(meth) acryloyloxyethylammonium chloride, N,N,N-triethyl-N-(meth)acryloyloxyethylammonium chloride, 2-hydroxy-3-(meth)acryloyloxypropyl trimethyl ammonium chloride], and monomers as mentioned in British patent specification No. 1,034,296.

Suitable monomers which become water-soluble by hydrolysis, for use in this invention instead of or in conjunction with the water-soluble monomers, include monoethylenically unsaturated compounds having at least one hydrolyzable group, such as ester, amide and nitrile groups. Such monomers having an ester group include for example, lower alkyl ($C_1$–$C_4$) esters of monoethylenically unsaturated carboxylic acids, such as methyl (meth)acrylate, ethyl (meth) acrylate and 2-ethylhexyl (meth)acrylate; and esters of monoethylenically unsaturated alcohols [vinyl esters, (meth)-allyl ester, etc.], such as vinyl acetate and (meth)allyl acetate. Suitable nitrile group-containing monomers include (meth)acrylonitrile.

Among these monomers having a polymerizable double bond which are water-soluble or become water-soluble by hydrolysis, water-soluble monomers which do not need hydrolysis after polymerization are preferred from the viewpoint of providing an easy process for producing water-absorbing resins. Further, from the viewpoint of providing water-absorbing resins having a high water-absorbence, the preferred water-soluble monomers are carboxyl group-containing monomers such as (meth)-acrylic acid and maleic acid anhydride; carboxylic acid salt group-containing monomers such as sodium (meth)acrylate, trimethylamine (meth) acrylate and triethanolamine (meth)acrylate, and quaternary ammonium salt group-containing monomers such as N,N, N-trimethyl-N-(meth)acryloyloxyethylammonium chloride. Most preferred superabsorbent forming monomers in the present invention include, for example, acrylic acid, methacrylic acid, maleic acid, fumaric acid, crotonic acid, sorbic acid, itaconic acid, cinnamic acid, vinyl sulfonic acid, allyl sulfonic acid, vinyl toluene sulfonic acid, styrene sulfonic acid, sulfo(meth)acrylate, sulfopropyl(meth)acrylate, 2-acrylamide-2-methylpropane sulfonic acid, 2-hydroxyethyl(meth)acryloylphosphate, phenyl-2-acryloyloxyethylphosphate, the sodium, potassium and ammonium salts thereof, maleic anhydride and combinations thereof. It is also preferred that the superabsorbent forming monomer in the sprayable blend is at least partially neutralized, most preferably neutralized to a level of from 1 to 100 mole percent, more preferably from 10 to 80 mole percent, and most preferably from 15 to 75 mole percent. Most preferably, the superabsorbent forming monomer is partially neutralized acrylic acid.

The superabsorbent forming monomers are present in the sprayable blends at a level of from about 15 to 50 percent by weight, preferably from 17 to 40 percent by weight, most preferably from 20 to 35 percent by weight. If the level of superabsorbent forming monomer in the sprayable blend is too low, the resulting web is likely to have poor performance characteristics. Within the preferred ranges, the conversion of superabsorbent forming monomer into polymer, when subjected to polymerization conditions, is generally much better. Also, increasing the relative amount of superabsorbent forming monomer in the sprayable blend generally reduces the amount of water in the sprayable blend. This is beneficial since it requires time, energy and expense to remove additional water from the final web. When partially neutralized acrylic acid is used as the superabsorbent forming monomer, e.g. 75% neutralized, it is preferred to use no more than 38% by weight of the partially neutralized acrylic acid in the sprayable blend.

Superabsorbent Polymer Particles

Superabsorbent polymer particles are lightly crosslinked polymers capable of absorbing several times their own weight in water and/or saline. Superabsorbent polymer particles can be made by any conventional process for preparing superabsorbent polymers and are well known to those skilled in the art. Suitable processes for preparing superabsorbent polymer particles include the processes described in U.S. Pat. Nos. 4,076,663; 4,286,082; 4,654,039 and 5,145,906 which describe the solution polymerization method and U.S. Pat. Nos. 4,340,706; 4,497,930; 4,666,975; 4,507,438 and 4,683,274 which describe the inverse suspension polymerization method, the disclosures of which are hereby incorporated by reference. Preferred superabsorbent polymer particles have an average particle size which is small enough so that the particles do not clog the spray equipment, preferably below about 150 microns, more preferably below about 100 microns. Such particle size can be obtained directly as a result of the polymerization process, or superabsorbent polymers can be sieved, ground, pulverized, attritted or a combination thereof to achieve superabsorbent polymer particles having the desired average particle size.

The superabsorbent polymer particles are present in the sprayable blends at a level of from about 1 to 20 percent by weight, preferably from 2 to 15 percent by weight, most preferably from 5 to 10 percent by weight. It has been observed that if the level of superabsorbent polymer particles is too high, premature polymerization can occur in the sprayable blend even in the absence of any other initiators.

Superabsorbent polymer particles useful in the present invention are prepared from one or more monoethylenically, unsaturated, water soluble carboxyl or carboxylic acid anhydride containing monomers and the alkali metal and ammonium salts thereof wherein said monomers comprise 50 to 99.9 mole percent of said polymer. Exemplary monomers include acrylic acid, methacrylic acid, maleic acid, fumaric acid, maleic anhydride and the sodium, potassium and ammonium salts thereof. The preferred monomer is acrylic acid.

Monoethylenically, unsaturated monomers are polymerized in the presence of an internal crosslinking compound to provide a lightly crosslinked base polymer wherein the crosslinking is substantially uniform throughout the polymer particles. These internal crosslinkers are well known in the art. Suitable crosslinkers are those compounds having two or more groups capable of reacting with the monoethylenically unsaturated monomers and which are at least partially water soluble or water dispersible, or at least partially soluble or dispersible in an aqueous monomer mixture. The internal crosslinking compound may be selected from a polyunsaturated monomer such as divinylbenzene, a compound having at least two functional groups which are reactive with the monoethylenically unsaturated monomer such as ethylenediamine, a compound having at least one unsaturated bond and at least one reactive functional group such as glycidyl acrylate.

Exemplary internal crosslinkers are: tetraallyloxyethane, N,N'-methylene bisacrylamide, N,N'-methylene bismethacrylamide, triallylamine, trimethylol propane triacrylate, glycerol propoxy triacrylate, divinylbenzene, N-methylol acrylamide, N-methylolmethacrylamide, glycidyl methacrylate, polyethylene polyamines, ethyl diamine, ethyl glycol, glycerine and the like. Preferred internal crosslinking monomers are those containing at least two allyl groups, most preferably three or four allyl groups. Preferred internal crosslinkers are tetraallyloxyethane and triallyl ether of pentaerythritol. The amount of internal crosslinker employed in the invention will depend on the internal crosslinker and the polymerization method. Generally the amount of internal crosslinker will vary from about 0.005% to about 1.0 mole percent based on moles of ethylenically unsaturated monomer.

Optional components used in the preparation of the superabsorbent polymer particles are water soluble hydroxy group containing polymers, such as polysaccharides and vinyl or acrylic polymers. Examples of water soluble polysaccharides are starches, water soluble celluloses and polygalactomannans. Suitable starches include the natural starches, such as sweet potato starch, potato starch, wheat starch, corn starch, rice starch, tapioca starch and the like. Processed or modified starches, such as dialdehyde starch, alkyl-etherified starch, allyl-etherified starch, oxylalkylated starch, aminoethyl-etherified starch, and cyanomethyl-etherified starch are also suitable. Polyvinyl alcohol and polyvinyl alcohol copolymers are also suitable.

The water-soluble celluloses useful in this invention are those obtained from such sources as wood, stems, bast, seed fluffs and the like which are then deriviatized to form hydroxyalkyl cellulose, carboxymethyl cellulose, methyl cellulose and the like.

Suitable polygalactomannans are guar gum and locust bean gums as well as their hydroxyalkyl, carboxyalkyl, and aminoalkyl derivatives. Water soluble vinyl and acrylic polymers include polyvinyl alcohol and poly(hydroxyethyl acrylate). The preferred polysaccharide for use in this invention is natural starch, such as wheat starch, corn starch and alpha starches. These optional preformed hydroxy containing polymers may be used in an amount from about 1–15 percent, preferably about 1 to 10 percent, most preferably about 1–5 percent.

The superabsorbent polymer particles useful in the present invention may be prepared by well known polymerization methods. The polymerization reaction is conducted in the presence of redox initiators and thermal initiators. The redox initiators can be used as the primary initiator with the thermal polymerization initiators being used if desired to reduce the free monomer content of the final polymerization product below 0.1 percent by weight. Optionally, thermal initiators or redox initiators may be used as the sole initiator system. Examples of different initiator systems are found in U.S. Pat. No. 4,497,930 which discloses a two component initiator system comprising a persulfate and a hydroperoxide and U.S. Pat. No. 5,145,906 which discloses a three component initiator system; i.e. redox system plus thermal initiator.

Any of the well known water soluble reducing agents and oxidizing agents can be used in this invention as the redox initiator. Examples of reducing agents include such compounds as ascorbic acid, alkali metal sulfites, alkali metal bisulfites, ammonium sulfite, ammonium bisulfite, alkali metal hydrogen sulfite, ammonium hydrogen sulfite, ferrous metal salts, e.g., ferrous sulfates, sugars, aldehydes, primary and secondary alcohols, and the like.

Oxidizing agents include such compounds as hydrogen peroxide, alkali metal persulfates, ammonium persulfate, alkylhydroperoxides, peresters, diacryl peroxides, silver salts, and the like. A particularly preferred redox initiator pair is ascorbic acid and hydrogen peroxide. The reducing agent is used in an amount of about $2\times10^{-5}$ to about $2.0\times10^{-2}$ mole percent based on moles of acrylic acid. The amount of oxidizing agent used will vary from about $2\times10^{-3}$ to about 1.1 mole percent, based on moles of acrylic acid.

In order to ensure complete polymerization of the unsaturated monomer and the crosslinking monomer, a thermal initiator can be included in the polymerization process. Useful thermal initiators are the "azo" initiators, i.e. compounds which contain the —N═N— structure. Any of the azo compounds which have solubility in water or in a monomer-water mixture and which have a 10 hour half life at 30° C. or above can be used. Examples of useful azo initiators are 2,2'-azobis(amidino) propane dihydrochloride, 4,4'-azobis (cyanovaleric acid), 4,4'-butylazo-cyanovaleric acid, 2,2'-azobis(isobutyronitrile ), 2,2'-azobis(2-(2-imidazole-2-yl))propane dihydrochloride, and the like. Other thermal initiators include the persulfates and hydroperoxides when used in the absence of a reducing agent e.g., sodium, potassium and ammonium persulfates, t-butylhydroperoxide and the like. A preferred azo initiator for use in this invention is 2,2'-azobis(amidinopropane) dihydrochloride. The thermal initiators are used in the amount of 0 to about 1 mole percent based on the weight of unsaturated monomer.

The superabsorbent polymer may be prepared by the solution or the inverse suspension polymerization method or any suitable bulk polymerization method. The solution polymerization and inverse polymerization methods are well known in the art; see for example U.S. Pat. Nos. 4,076,663; 4,286,082; 4,654,039 and 5,145,906 which describe the solution polymerization method and U.S. Pat. Nos. 4,340,706; 4,497,930; 4,666,975; 4,507,438 and 4,683,274 which describe the inverse suspension polymerization method. The teachings of these patents are hereby incorporated by reference.

In the solution polymerization method, the water soluble monomer is polymerized at a monomer concentration from about 5 to about 30 percent in aqueous solution at a temperature from about 5° C. to about 150° C. depending upon the polymerization initiator system. A detailed description of the solution polymerization method is given in U.S. Pat. No. 5,145,906; the teachings of which are hereby incorporated by reference.

In the inverse suspension polymerization process, the unsaturated monomer in an aqueous solution (about 35 to 60 percent monomer to 65 to 40 percent water) is dispersed in an alicyclic or aliphatic hydrocarbon suspension medium in the presence of a dispersing agent such as a surfactant or protective colloid such as polyvinyl alcohol. A surfactant having a HLB value of 8–12 such as a sorbitan fatty acid ester ether may employed as the dispersing agent. The inverse suspension polymerization method is described in detail in U.S. Pat. No. 4,340,706; the teachings of which are hereby incorporated by reference.

The carboxylic acid groups of the unsaturated monomer used in the polymerization may be neutralized prior to or subsequent to the polymerization. Suitable neutralizing agents include an alkali such as sodium hydroxide, ammonium hydroxide, potassium hydroxide or the like, and the appropriate degree of neutralization is 50–98 mole percent; preferably 60–75 percent. The degree of neutralization is preferably at least 50 mole percent. Low neutralization levels (less than 50 mole percent) tend to result in superabsorbent polymers having low absorbency properties.

The polymer is prepared by either the solution or inverse suspension polymerization method dried and screened to provide a superabsorbent particle with an appropriate particle size distribution and particle shape. Generally the superabsorbent particle size distribution should be between 10 and 300 microns, preferably between 45 and 150 microns. Large particles over 300 microns are undesired since they may tend to clog the nozzle of spray equipment used to spray the sprayable blend. Also, large particles may cause the absorbent article to have an abrasive feel.

Although many of the conventional teachings in this area prefer to avoid the use of small particle size superabsorbent polymer particles, we have found that these particles work quite well in the present invention. Superabsorbent polymer particles having particle sizes in the range of from 10 to 300 microns tend to work well with the spray equipment, produce sprayable blends having manageable viscosities, and result in absorbent articles having discrete superabsorbent particles attached to the fibrous web.

The superabsorbent polymer particles described above may optionally be further treated with a crosslinker solution containing from about 0.5 to about 3.5 weight percent water, from about 1.0 to 2.5 weight percent of a water miscible solvent selected from a $C_3$ to $C_6$ diol and a crosslinker having at least two functional groups that can react with the carboxyl, carboxylate or other reactive groups in the superabsorbent polymer chain to crosslink the polymer chains on or in the vicinity of the surface of the superabsorbent polymer particles. The term "diol" is intended to mean a dihydroxy aliphatic compound which may be a linear or branched compound, (a glycol). The term "surface crosslinking" used in this description and the claims hereof is used to describe this process of crosslinking the polymer chains on or in the vicinity of the particle's surface. The terms, "surface crosslinker" and "surface crosslinker solution" are likewise used to describe the crosslinking compound and the solution used to effect this surface crosslinking process. The crosslinking compound is used in an amount of from about 0.01 to about 3 weight percent, preferably 0.1% to 1.5% and most preferably about 0.25% to 1% based upon the weight of the superabsorbent polymer. The surface crosslinker may be selected from diglycidyl ethers, haloepoxy, isocyanate, aziridinyl, azetidinium group containing compounds, polyamine, polyamine-polyamide, polyamine-epichlorohydrin adducts and amine-polymer-epichlorohydrin adducts and the like. Preferred crosslinkers are the higher molecular weight diglycidyl ether compounds of at least 200 and the polymeric-epichlorohydrin adducts having a molecular weight average in excess of 2000.

Exemplary surface crosslinkers are poly (ethylene glycol) diglycidyl ethers, poly (propylene glycol) diglycidyl ethers, epichlorohydrin substituted compounds, methyl-epichlorohydrin substituted compounds, hexamethylene diisocyanate, triethylene triamine, polyethylene amine, 2,2-bishydroxymethylbutanol-tris[3-(1-azindinyl)propionate], polyamine epichlorohydrin adducts, polyethylene-polyamine-epichlorohydrin adducts, and the like.

When used, the preferred surface crosslinkers are the higher molecular weight diglycidyl ether compounds, polyamide (polyamide-polyamine) epichlorohydrin adducts, polyamine epichlorohydrin adducts and amine polymer epichlorohydrin adducts. Polyamide-epichlorohydrin adducts are prepared by reacting epichlorohydrin with the polycondensation product of a polyalkylene polyamine with a polycarboxylic acid such as diethylene triamine with a dibasic acid such as adipic acid. Polyamine epichlorohydrin adducts are made by condensing a polyalkylene polyamine directly with epichlorohydrin. These adducts include polyalkylene polyamines which are linked together with dihalides to form higher polyamines before reacting them with epichlorohydrin. Amine polymer epichlorohydrin adducts include resins in which the monomeric amine is polymerized to a polyamine precursor which is then alkylated and reacted with epichlorohydrin. They include amines substituted polymers of vinyl, allyl, acrylate or epoxy monomers. The epichlorohydrin adducts whether the polymer is a polyamide, a polyamine or an amine polymer react with the epichlorohydrin by different routes. If the amino group in the polymer chain is a primary amine, two epichlorohydrin molecules reacted with the nitrogen and form a disubstituted chlorohydroxypropyl substituted amine group. Secondary amine groups react with epichlorohydrin to form a tertiary aminochlorohydrin group which cyclizes to form a reactive 3-hydroxyazetidinium salt moiety. This is a preferred reactive group. Tertiary amine groups react with epichlorohydrin to form a glycidyl; (2,3 epoxypropyl) ammoniurn salt. Preferably the reactive group is an azetidinium moiety. However, these adducts may contain a mixture of chlorohydroxypropyl, epoxy and azetidinium groups. Preferably the epichlorohydrin adducts have a molecular weight of at least 2,000; preferably 300,000 to 500,000 and wherein at least 50 mole percent of the reactive groups in the adduct are the azetidinium group. A preferred polymer is one in which about 90% of the substitution is in the form of an azetidinium group and about 10% as an epoxide group. Exemplary products are Reten.RTM. 204LS and Kymeme.RTM. 736 epichlorohydrin adducts; available from Hercules Inc., Wilmington, Del. These products are sold as an aqueous solution of the reactive epichlorohydrin adduct. The Reten.RTM. 204LS product is available as a 15% aqueous solution and the Kymeme.RTM. 736 product as a 38% aqueous solution.

The surface crosslinker solution should have a surface tension not greater than about 55 dynes per cm; preferably not greater than about 50 dynes per cm; e.g. about 40 to about 50 dynes per cm. In the event the surface tension of the crosslinker solution is higher than about 55 dynes per cm; the surface crosslinked polymer has inferior absorbency as evidenced by a low 0.6 psi AUL value. While not being bound to any theory, it is believed that when the surface tension of the crosslinker solution is higher than about 55 dynes per cm, the solution is not uniformly distributed on the surface of the polymer particles and a lower absorbency value results. Optionally, a surfactant may be used to reduce the surface tension of the crosslinker solution.

The desired surface tension is achieved by adding the $C_3$ to $C_6$ dihydroxy compound to water component of the crosslinker solution to achieve a surface tension below about 55 dynes/cm range. The amount of each solvent is determined by simple experimentation. Generally the crosslinker has a negligible effect on the surface tension of the crosslinker solution. The diols useful in the invention are propylene glycol, butylene glycol, pentanediol and hexanediol. Ethylene glycol was found to be an undesired solvent because it tends to swell the superabsorbent polymer particles and their surfaces becomes tacky which results in undesired particle agglomeration. In addition, ethylene glycol is undesirable because of its toxicity and biodegradability properties. The $C_3$ to $C_6$ diol is used in an amount of from about 1 percent by weight to about 2.5 percent by weight based upon the weight of superabsorbent polymer; preferably about 1 to about 2 percent by weight. The water component of the crosslinker solution comprises about 0.5 to 3.5 percent by water based upon the weight of the polymer, preferably about 1.5 to 2.0 percent.

The total amount of crosslinker solution used depends upon the type of equipment and the method used to coat the base polymer with the surface crosslinking solution. Generally the amount of crosslinker solution should be about 1.5% minimum based on the weight of the polymer. The crosslinker solution is applied to the base polymer particles in a manner such that the solution is uniformly distributed on the surface of the base polymer particle. Any of the known methods for dispersing a liquid can be used; preferably by dispersing the crosslinker solution into fine droplets; e.g. by use of a pressurized nozzle or a rotating disc. Uniform crosslinker dispersion on the base polymer can be achieved in a high intensity mechanical mixer or a fluidized mixture which suspends the base polymer in a turbulent gas stream. Methods for the dispersion of a liquid onto the superabsorbent base polymer's surface are known in the art; see for example U.S. Pat. No. 4,734,478; the teachings of which are hereby incorporated by reference; in particular column 6, line 45 to column 7, line 35.

Exemplary commercially available equipment for conducting the crosslinker solution dispersion step of the invention are high speed variable intensity paddle mixers such as the "Turbulizer" mixer of the Bepex Corporation, Rolling Meadows, Ill. or the high speed variable intensity vertical mixer sold by Bepex under the tradename, "Turboflex". These machines are generally operated in a continuous manner using a short residence time in the order of 2 seconds to 2 minutes, typically 2–30 seconds. Dispersion may be effected batchwise in a high intensity mixer such as a Henschel mixer or in liquid-solid V-blender equipped with a liquid dispersion device. In any event, whether a batchwise or continuous dispersion method is used, simple experimentation can be conducted to determine the best process conditions for the particular machine employed in the process. Preferably, the surface crosslinker is coated onto the polymer particles under high intensity mixing conditions.

After effecting dispersion of the surface crosslinker on the base polymer particle the crosslinking reaction is effected and the polymer particle dried. The crosslinking reaction may be effected at a temperature from about 70° C. to about 180° C.

Initiators

The sprayable blend used in the present invention contains one or more initiators. Suitable initiators include the initiators and initiator combinations described above as being useful in the production of superabsorbent polymer particles. In addition, it may be desirable to use initiators designed to decompose when subjected to ultraviolet light and/or electron-beam ("e-beam") irradiation. Preferred initiators include water-soluble azo compounds such as 2,2'-azobis(2-(2-imidazole-2-yl))propane dihydrochloride and 2,2'-azobis(amidino) propane dihydrochloride, water soluble benzophenones such as 4-benzoyl-N,N,N-trimethylbenzenemethanaminium chloride, 2-hydroxy-3-(4-benzoylphenoxy)-3-N,N,N-trimethyl-1-propanaminium chloride monohydrate, 2-hydroxy-3-(3,4-dimethyl-9-oxo-9H-thioaxanthon-2-yloxy)-N,N,N-trimethyl-1-propaniminium chloride, 2-hydroxy-1-[4-(hydroxyethoxy)phenyl]-2-methyl-1-propanone, 2-hydroxy-2-methyl-1-phenyl-propan-1-one, and 4-benzoyl-N,N-dimethyl-N-[2-(1-oxo-2-propenyl)oxy]ethylbenzenemethaniminium chloride. In general, the sprayable blend contains one or more initiators at a level sufficient to initiate polymerization of the superabsorbent-forming monomer in the sprayable blend. The sprayable blend contains one or more initiators at a level sufficient to result in the complete polymerization of the superabsorbent forming monomer in the sprayable blend, generally at a level within the range of from 0.01 to 5.0, most preferably at a level of from 0.2 to 2.0 percent by weight of the superabsorbent forming monomer in the sprayable blend. When using a combination of initiators in the sprayable blend, such as redox package, it is possible to incorporate one of the initiators, such as the reducing agent, into the sprayable blend along with the other components of the sprayable blend and incorporate one or more additional initators, such as an oxidizing agent, into the sprayable blend just before the sprayable blend exits the nozzle of the spray equipment being used to spray the sprayable blend onto the fibrous web. A particularly preferred combination of initiators includes both an azo initiator and 2-hydroxy-1-[4-(hydroxyethoxy)phenyl]-2-methyl-1-propanone.

Water

In addition to the superabsorbent polymer particles, superabsorbent-forming monomer and one or more initiators, the sprayable blend contains water. Generally, the sprayable blend contains sufficient water to render the Brookfield viscosity of the sprayable blend in the range of from 20 to 400 centipoises, more preferably from 30 to 150 centipoises, most preferably from 40 to 100 centipoises. The level of water in the sprayable blend is generally in the range of from 40 to 80 percent by weight, more preferably from 50 to 60 percent by weight of the sprayable blend.

Crosslinker

It is generally desirable to include in the sprayable blend, one or more crosslinkers. It is particularly preferred to use one or more crosslinkers in the sprayable blend when the sprayable blend contains thermal, redox and or UV initiators. Suitable crosslinkers include those described above for the superabsorbent polymer particles. Preferred crosslinkers include ethoxylated and propoxylated trimethylolpropanetriacrylate derivatives such as SR-9035 and SR-492 available from Sartomer Co., Inc. of Exton, Pa. When used, the one or more crosslinkers are present in the sprayable blend at a level of from 0.05 to 5.0 percent based on the weight of superabsorbent forming monomer.

Process of the Invention

In the process of the present invention, a sprayable blend is prepared by combining superabsorbent forming monomer, super absorbent polymer particles, water and initiator. Although the order of combining these materials is not particularly important, for safety reasons it is preferred to add the initiator last. The amounts of the individual components of the blend are set forth above and are generally selected so that the Brookfield viscosity of the sprayable blend is in the range of from 20 to 400 centipoises, more preferably from 30 to 150 centipoises, most preferably from 40 to 100 centipoises. Many factors will influence the viscosity of the sprayable blend, including the chemical nature and size of the superabsorbent polymer particle, the extent of neutralization of the superabsorbent polymer particles, the extent of neutralization of the one or more superabsorbent forming monomers, and the concentration of the superabsorbent polymer particles.

After the sprayable blend has been prepared, it is sprayed onto a fibrous web. As used herein, spraying is intended to include any suitable means for generating and delivering droplets of liquid. The spraying can be achieved by any conventional spray equipment. The equipment can be airless, air-assisted airless or can utilize pressurized air. One or more inert gases, such as nitrogen, argon or helium, may be substituted for some or all of the air to assist in the removal of oxygen from the sprayable blend during the spraying process. The sprayable blend is sprayed onto a fibrous web to 20 to 400 grams per square meter ("gsm") of superabsorbent polymer particles on a dry weight basis, preferably from 40 to 300 gsm of superabsorbent polymer particles on a dry weight basis, most preferably from 60 to 150 gsm of superabsorbent polymer particles on a dry weight basis. The spray equipment should be adjusted to vary the droplet size of the spray taking into account such factors as the size of the superabsorbent polymer particles in the sprayable blend and the desired particle size of superabsorbent polymer particles on the final product.

The WEB

Suitable fibrous webs for the present invention include those made using synthetic polymeric fibers. The synthetic polymeric fibers may be formed from any polymeric material capable of forming fibers which fibers can be formed into a fibrous web. Suitable polymeric material from which the synthetic polymeric fibers may be formed include polyolefins, such as polyethylene, polypropylene, and the like; polyesters such as polyethylene terephthalate and the like; polyamides such as nylon 6, nylon 6,6, poly (iminocarboxylpentamethylene) and the like; acrylics, and modified cellulosic material, such as cellulose acetate and rayon; as well as mixtures and copolymers thereof.

The synthetic polymeric fibers may be formed by meltblowing, through a spunbond process, by extrusion and drawing, or other wet, dry and melt spinning methods known to those skilled in the art. The synthetic polymeric fibers from which the web is formed may have a discrete length or may be substantially continuous. For example, if the synthetic polymeric fibers are formed by meltblowing, the fibers may be substantially continuous (few visible ends). If the fibers are formed by extrusion and drawing to produce a tow, the tow may be used as produced or cut into staple fibers having a length, for example, of from about 25 millimeters to about 75 millimeters or short cut into lengths of from about 1 millimeter to about 25 millimeters. The synthetic polymeric fibers may suitably have a maximum cross-sectional dimension of from about 0.5 micrometer to about 50 micrometers as determined by microscopic measurement using an optical microscope and a calibrated stage micrometer or by measurement from Scanning Electron photomicrographs.

The fibrous webs may be formed directly through a spunbond or meltblown process, or by carding or air-laying staple or short cut fibers. Other methods of forming fibrous webs known to those skilled in the art may be suited for use in the present invention. The web may subsequently be bonded to enhance structural integrity. Methods of bonding fibrous webs are known to those skilled in the art and include thermal bonding, point bonding, powder bonding, ultrasonic bonding, chemical bonding, mechanical entanglement, and the like. The fibers may be homogenous fibers or may be a core/sheath or side-by-side fibers known to those skilled in the art as bicomponent fibers.

The fibrous web may be formed from a single type of synthetic polymeric fiber or may contain synthetic polymeric fibers formed from different polymeric materials, having different fiber lengths or maximum cross-sectional dimensions. For example, the web may comprise a mixture of (1) bicomponent fibers having a polyethylene sheath and a polypropylene core which bicomponent fibers have a maximum cross-sectional dimension of about 20 micrometers and a length of about 38 millimeters and (2) polyester fibers (polyethylene terephthalate) having a maximum cross-sectional dimension of about 25 micrometers and a length of about 38 millimeters. Fibers 1 and 2 may be combined in a weight ratio of from 1:99 to 99:1. The fibers may be uniformly mixed or may be concentrated at opposite planar surfaces of the fibrous web.

The web suitably comprises from about 10 to 100 weight percent, beneficially of from about 20 to 100 weight percent, preferably of from about 25 to 100 weight percent, and most preferably of from about 50 to 100 weight percent synthetic polymeric fibers. In addition to the synthetic polymeric fibers, the web may contain from about 90 to 0 weight percent of a nonsynthetic polymeric fiber such as wood pulp fluff cotton linters, cotton, and the like.

In one preferred embodiment, the web contains synthetic polymeric fibers which are formed from a polymeric material having a high wet modulus. The importance of the modulus of a material is discussed in the book "Absorbency" edited by P. K. Chatterjee (Elsevier, N.Y., 1985). A polymeric material will be considered to have a high wet modulus when it has a wet modulus greater than about 80 percent of its dry modulus as determined by ASTM (American Society for Testing and Materials) test method D 2101-91 using modified gauge lengths. It is often desired to form the synthetic polymeric fibers of the web from a polymeric material having a high wet modulus because such materials generally form fibrous webs which possess a relatively high degree of wet resiliency. The wet resilience of a fibrous web is related to the pore structure (while under a load) of the fibrous web. As will be discussed in greater detail below, it is often desired that the web have a relatively high degree of wet resilience.

The pore structure (while under a load) of a fibrous structure formed from fibers of a polymeric material will, as discussed above, relate to the wet and/or dry modulus of the constituent fibers. Wet modulus of the constituent fibers should be considered for fibers that may likely be wetted during use. For the purposes of estimating the effect of load on the pore structure of a fibrous structure formed from fibers of a polymeric material the tensile modulus of the fiber which can be related to the flexural rigidity of the fiber as shown in the book "Physical Properties of Textile Fibers" by W. E. Morton and J. W. S. Hearl (The Textile Institute, London, 1975) can be used.

As a general rule, the polymeric materials from which the synthetic polymeric fibers of the web are formed will be inherently hydrophobic. As used herein, the term "hydrophobic" describes a material which has a contact angle of water-in-air of greater than 90 degrees. The term "hydrophilic" refers to a material which has a water-in-air contact angle of less than 90 degrees. The water-in-air contact angle is suitably determined as set forth in the book "Absorbency" edited by P. K. Chatterjee (Elsevier, N.Y., 1985). As used herein, a polymeric material will be considered to be "inherently" hydrophobic or hydrophilic when the polymeric material, free from any surface modifications or treatments, e.g., surface active agents, spin finishes, blooming agents, etc., is hydrophobic or hydrophilic, respectively.

When the synthetic polymeric fibers of the web are formed from a polymeric material which is inherently hydrophobic, it is often desirable to treat the fibers with a surface modifying material to render the surface of the fiber hydrophilic. For example, a surfactant may be applied to the fibers.

The web suitably has a basis weight of from about 20 to about 200, beneficially of from about 30 to about 150, and preferably of from about 35 to about 125 grams per square meter.

The web suitably has a density of from about 0.005 to about 0.12, beneficially of from about 0.008 to about 0.1, and preferably of from about 0.01 to about 0.08 gram per cubic centimeter.

The fibrous web may also comprise hydrophilic fibers. The hydrophilic materials may be inherently hydrophilic such as cellulosic fibers such as wood pulp fluff, cotton linters, and the like; regenerated cellulose fibers such as rayon; or certain nylon copolymers such as poly (pentamethylenecarbonamide) (nylon-6)/polyethylene oxide. Alternatively, the hydrophilic fibers may be hydrophobic fibers which have been treated to possess a hydrophilic surface. For example, the fibers may be formed from a polyolefin material which is subsequently coated with a surface active agent such that the fiber itself is hydrophilic as described herein. Other methods of hydrophilizing fibers formed from hydrophobic materials are known and suited for use in the present invention.

Methods of providing inherently hydrophilic fibers such as wood pulp fluff are known. So to are methods of providing regenerated cellulosic fibers such as rayon. Hydrophobic fibers which can be treated to possess a hydrophilic surface are suitably formed by processes known to those skilled in the art. If the hydrophilic fibers are hydrophobic fibers which have been treated to possess a hydrophilic surface, the fibers will suitably have a fiber length and maximum cross-sectional dimension as set forth above. If the hydrophilic fibers are inherently hydrophilic such as wood pulp fluff, rayon, cotton, cotton linters and the like, the fibers will generally have a length of from about 1.0 millimeters to about 50 millimeters and a maximum cross-sectional dimension of from about 0.5 micrometers to about 100 micrometers.

The fibrous web suitably comprises from about 10 to 100 weight percent, beneficially from about 30 to 100 weight percent, and preferably from about 55 to 100 weight percent of hydrophilic fibers, preferably inherently hydrophilic fibers. In addition to the hydrophilic fibers, the web may contain from about 90 to 0 weight percent of a high wet modulus, preferably inherently hydrophobic fibers. The web may be formed from a single type of hydrophilic fiber or may contain hydrophilic fibers having different compositions, lengths and maximum cross-sectional dimensions.

In one preferred embodiment, the web is formed from air laid cellulosic fibers such as wood pulp fluff. Wood pulp fluff fibers are preferred for use due to their ready availability and due to the fact that the fibers are relatively inexpensive compared to synthetic polymeric fibers.

The web suitably has a basis weight of from about 20 to about 200, beneficially of from about 50 to about 150, and preferably of from about 25 to about 125 grams per square meter.

The web suitably has a density of from about 0.04 to about 0.20, beneficially of from about 0.06 to about 0.16, and preferably of from about 0.08 to about 0.14 gram per cubic centimeter.

Curing/Polymerizing

After the sprayable blend has been sprayed onto the fibrous web, this composite is subjected to conditions under which the superabsorbent forming monomer from the sprayable blend will polymerize. Depending upon the type of initiator used in the sprayable blend, these conditions may include, for example, subjecting the fibrous web sprayed with the sprayable blend to heat, ultraviolet radiation, e-beam radiation, or a combination thereof. Furthermore, the composite can be subjected to static or continuous conditions such as by moving the composite along a conveyor through regions of radiation or heat.

For thermal curing there are no particular limitations on the type of reaction vessel used. For batch polymerizations, sprayed webs may be cured in an oven in an air or inert atmosphere, and optionally under vacuum. In the case of a continuous process, the web may be passed through a dryer, such as an infrared ("IR"), through air or the like. The polymerization temperature can vary depending on the thickness of the substrate, the concentration of monomer and the type and amount of thermal initiator used in the sprayable blend. The polymerization is typically in the range of from 20° C. to 150° C. and preferably in the range of from 40° C. to 100° C. The polymerization time depends on the polymerization temperature, but is typically several seconds to 2 hours and preferably several seconds to 10 minutes. After polymerization is completed, the web can then be dried to the desired moisture content.

UV curing of webs coated with the sprayable blends may be conducted by the use of a conventional UV lamp. The conditions under which the irradiation is conducted, such as radiation intensity and time may differ depending on the type of fibrous substrate used, the amount of monomer applied to the substrate and the like. However, irradiation is generally conducted using a UV lamp with an intensity in the range of from 100 to 700 watts per inch ("W/in"), preferably in the range of from 400 to 600 W/in for 0.1 seconds to 10 minutes, with the distance between the UV lamp and the substrate being 2 to 30 centimeters. The irradiation of the composite with ultraviolet rays may be conducted under vacuum, in the presence of an inorganic gas, such as nitrogen, argon, helium and the like, or in air.

The temperature during irradiation is not critical, and the irradiation of the sprayed web can be satisfactorily conducted at room temperature.

Electron beam curing can be accomplished using a commercially available electron beam accelerator, such as the Electrocurtain® CB 175 (Energy Sciences, Inc., Wilmington, Ma.). Accelerators operating in the 150 to 300 kilovolt range are acceptable. The beam current on such systems, typically 1 to 10 milliamperes, can be adjusted to obtain the desired dose of ionizing radiation. The ionizing radiation dose employed will vary somewhat, depending on factors such as the presence or absence of crosslinking monomers, desired degree of polymerization of the polymer, degree of cross-linking desired, and the like. In general, it is desirable to irradiate the coated web with doses from about 1 to 16 megarads, more preferably 2 to 8 megarads. Particularly when using lower doses, it is desirable to purge oxygen from the sprayable blend (as by bubbling nitrogen through the solution). The maximum dose would be that dose at which degradation of the fibers begins.

After irradiation, the coated web may be dried to remove water by such means as forced air ovens, infrared lamps and the like.

Acquisition Layer

The absorbent structures according to the present invention are suitable for use in disposable absorbent products such as diapers, training pants, adult incontinence products, feminine care products, wound dressings and the like. Methods of forming such absorbent products and the absorbent products formed thereby are known to those skilled in the art and are described, for example, in the following U.S. Pat. No. 4,944,735 issued Jul. 31, 1990 to Mokry; U.S. Pat. No. 4,798,603 issued Jan. 17, 1989, to Meyer et al.; U.S. Pat. No. 4,710,187 issued Dec. 1, 1987, to Boland et al.; U.S. Pat. No. 4,770,656 issued Sep. 13, 1988, to Proxmire et al.; and U.S. Pat. No. 4,762,521 issued Aug. 9, 1988, to Roessler et al.; the disclosures of which are incorporated herein to the extent they are consistent herewith.

The absorbent structures of the present invention suitably form an acquisition layer of a disposable absorbent product. Such an acquisition layer core is suitably sandwiched between, and in liquid communication with, a bodyside liner (also known as a top sheet), and an absorbent core atop a liquid impervious outer cover. In order to function well as an acquisition layer, an absorbent structure should exhibit rapid uptake of fluid, good transfer properties, good uptake upon repeated insults with fluid, and good skin compatibility.

The absorbent structures of the present invention exhibit these properties and also have further advantages. Because the absorbent structures of the present invention can be prepared with superabsorbent polymer particles that are at least partially neutralized, and because the superabsorbent forming monomer used in the sprayable blend can be at least partially neutralized, it is possible to control the pH of the resulting absorbent structure formed by polymerizing the sprayable blend sprayed onto the fibrous web. By controlling the pH of the absorbent structure, particularly within the range of from about 4.3 to about 5.5, several advantages can result. For example, an absorbent structure having a pH within that range should be compatible with skin, should exhibit reduced bacterial growth, should reduce fecal proteolytic activity and lipolylic enzymatic activity, should control odor and contain ammonia. The benefits associated with the control of pH in a top sheet of a disposable hygienic article are discussed, for example, in U.S. Pat. No. 4,657,537, the disclosure of which is hereby incorporated by reference. Similar benefits are expected to result from an acquisition layer having a pH in the range of from about 4.3 to about 5.5. Although the partial neutralization of the superabsorbent polymer particles and superabsorbent forming monomer will tend to reduce the overall absorptive capacity of the absorbent structure of the present invention, total absorptive capacity is not a critical feature when using the structures as an acquisition layer in a disposable hygiene product. Rather, the diminished total absorptive capacity contributes to the transfer properties which are beneficial in an acquisition layer.

It is further believed that the absorbent structures of the present invention perform well as acquisition layers in a disposable diaper because the swelling of the superabsorbent polymer particles is capable of expanding the fibrous web, particularly if the web were compressed, so that the interstitial pore volume of the web increases after an insult of liquid. This increase in the interstitial pore volume of the web contributes to the rapid uptake of fluids in the web. Accordingly, enhancing the speed at which the interstitial pore volume is generated, such as by the rapid swelling of the superabsorbent polymer particles, further contributes to the rapid uptake of fluids in the web. The free-swell expansion volume ("FSEV") test and the expansion volume under load ("EVUL") test described below are an indirect measure of the rate of formation of the interstitial pore volume in the web. In general, it is desirable to maximize the values of the FSEV and EVUL in designing a high performing superabsorbent article. At a minimum the absorbent structures of the present invention have free-swell expansion volumes and/or expansion volumes under load of at least about 0.1 milliliters within about 5 minutes, preferably within about 30 seconds, and most preferably within about 5 seconds. Preferably, the absorbent structures of the present invention have free-swell expansion volumes of at least about 0.5 milliliters within about 5 minutes, preferably within about 30 seconds, and most preferably within about 5 seconds. Most preferably, the absorbent structures of the present invention generally have free-swell expansion volumes of at least about 1.0 milliliters within about 5 minutes, preferably within about 30 seconds, and most preferably within about 5 seconds. Preferably, the absorbent structures of the present invention generally have expansion volumes under load of at least about 0.2 milliliters within about 5 minutes, preferably within about 30 seconds, and most preferably within about 5 seconds. Most preferably, the absorbent structures of the present invention generally have expansion volumes under load of at least about 0.3 milliliters within about 5 minutes, preferably within about 30 seconds, and most preferably within about 5 seconds.

The absorbent core comprises means for containing a high-absorbency material, and a high-absorbency material contained by such means for containing a high-absorbency material. The high-absorbency material is present in the absorbent structure in an amount of from about 50 to about 100, preferably of from about 60 to about 95, and most preferably of from about 70 to about 90 weight percent based on total weight of the absorbent core.

Means of containing high-absorbency materials are known to those skilled in the art. For example, the means for containing the high-absorbency material may comprise a fibrous web, a porous sponge-like material, a substrate to which the high-absorbency material is attached or adhered, multiple sheets of material between which the high-absorbency material is located, and the like. Any means of containing of the high-absorbency material is suited for use in the present invention.

As used herein, the term "high-absorbency material" refers to a water-swellable, generally water-insoluble material capable of absorbing at least about 10, desirably about 20, and preferably about 50 times or more its weight in water. The high-absorbency material may be formed from organic material, which may include natural materials such as agar, pectin, and guar gum, as well as synthetic materials such as synthetic hydrogel polymers. Synthetic hydrogel polymers include, for example, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyrridine, polyvinylamines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the materials substantially water insoluble. Crosslinking may, for example, be by irradiation or covalent, ionic, van der Waals, or hydrogen bonding. Suitable materials are available from various commercial vendors such as the Dow Chemical Company, BASF Corporation, Chemdal Corp., Nippon Shokubai., and Stockhausen Inc. The high-absorbency material may be in the form of particles, spheres, flakes, fibers, rods, films or any of a number of geometric forms. When in the form of particles or spheres, it may be desired that the particles or spheres have a maximum cross-sectional dimension of from about 10 micrometers to about 2000 micrometers, preferably from about 60 micrometers to about 1000 micrometers.

In one embodiment it is desired that the high-absorbency material have the ability to absorb a liquid while under a load. The ability of a high-absorbency material to absorb a liquid while under a load is quantified as the Absorbency Against Pressure (AAP) value. Specifically, the AAP value is the amount (in grams) of an aqueous solution containing 0.9 weight percent sodium chloride, a gram of the high-absorbency material can absorb in 60 minutes under a load of 0.3 pound per square inch. As a general rule, it is desired that the high-absorbency material have an AAP value of at least about 10, desirably at least about 15, and preferably at least about 25. A method by which the absorbency against pressure value is determined is set forth below in connection with the Examples.

The absorbent core suitably has a basis weight of from about 200 to about 1000, beneficially of from about 250 to about 750, and preferably of from about 300 to about 500 grams per square meter. The absorbent layer suitably has a density of from about 0.06 to about 0.40, beneficially of from about 0.12 to about 0.35, and most preferably of from about 0.15 to about 0.30 gram per cubic centimeter.

A further advantage of locating the acquisition layer between the body of a wearer and the absorbent layer is that the acquisition layer, may have a relatively dry feel even after it has been wetted. This is because the acquisition layer includes synthetic polymeric fibers, is resilient and may be more easily desorbed by the absorbent layer. Thus, a relatively dry surface may be presented for contacting a wearer's skin. In contrast, the absorbent layer including cellulosic or other inherently hydrophilic fibers can have a relatively wet feel. This wet surface is located remote from the body of a wearer and is spaced therefrom by the acquisition layer.

It is well known to those in the art of disposable hygienic products that the insertion of thick, lofty fabric structures between the topsheet and the absorbent core aids in the rate of uptake of fluid insults from the surface of the article. U.S. Pat. No. 5,364,382 discloses a number of key properties of these acquisition layers, such as the wet and/or dry modulus of the constituent fibers, the hydrophillicity of the fibers and resiliency of the fabric structure, that contribute to the ability of these materials to rapidly uptake fluids in an absorbent article. Such properties contribute to the acquisition layer's ability to: stay open under load, maintain void volume, resist collapse when wetted, enhance the desorption properties of the fabric, and preserve void volume capacity after successive insults of fluid.

One advantage of the absorbent articles of the present invention is the rate of formation of void volume following compression of the absorbent article. In many current, commercially manufactured absorbent products a considerable amount of pressure is applied during manufacture to produce an "ultrathin" product. Acquisition materials used in these current products have no real mechanism to reopen after being compressed other than the memory effects preserved within the fibers themselves. The incorporation of discrete superabsorbent particles into a fibrous web, as provided in the present invention, provides such a mechanism through the swelling of the superabsorbent particles following an insult of fluid. Two important performance parameters of an acquisition layer in a disposable hygienic article are (1) the degree of expansion and (2) the rate of expansion. Both of these parameters are indirectly measured by FSEV and EVUL. The degree of expansion is an indication of the pore volume available for fluid uptake (i.e. larger volume correlates with better performance) and by increasing the speed at which this pore volume is generated the likelihood of leakage upon insult is diminished. Both of these properties maybe be influenced by adjusting such parameters as: the degree loading of superabsorbent polymer particles on the web, the particle size of the superabsorbent polymer particles, the degree of swelling of the superabsorbent polymer particles, the degree of neutralization of the superabsorbent forming monomer in the sprayable blend, the degree of crosslinking and the like.

It has also been observed that webs, after being sprayed with a sprayable blend and subjected polymerization conditions, have other beneficial properties. As mentioned above, certain web materials are subjected to compression at one or more times during the construction of a disposable hygienic article such as a diaper. After a web material has been compressed, there is a tendency for the fibers to relax, and expand somewhat thereby increasing the thickness of the web. However, this relaxation phenomenon is much less pronounced in articles prepared in accordance with the present invention which tend to remain stably in a compact state until subjected to an insult of fluid.

Rewet and strikethrough testing of absorbent articles are common quality assurance tests used in the hygiene industry to measure surface dryness and the rate of fluid uptake, respectively, following successive fluid insults; therefore, these tests are useful for the evaluation of the performance of acquisition materials in absorbent products. A common undesirable trend seen among most commercially available diapers on the market today is the fact that strikethrough times tend to increase with successive doses of fluid during rewet testing. With conventional fluff-based absorbent structures the cellulosic fibers can lose resiliency and collapse when wetted. As a result, the liquid uptake rate of the wetted structures may become too low to adequately accommodate subsequent, successive fluid insults. Where absorbent gelling particles are incorporated between the fibers to hold them apart, the gelling particles swell and do not release the fluid. Swelling of the particles can then diminish the void volume of the absorbent structure and reduce the ability of the structure to rapidly uptake fluid. The degree to which the swelling of the absorbent gelling particle negatively impacts the rate of fluid uptake is dependent upon a number of factors such as the concentration of superbsorbent used in the absorbent core, the degree of cross-linking, the uniformity of the distribution of SAP within the structure, the particle size distribution, the hydrophobicity of the particle and the like. Each of these factors are easily controlled with the present invention and may be optimized to achieve the desired performance properties for a given absorbent article, particuliarly when used as an acquisition layer in an absorbent article. Examples 17–20, below, demonstrate some of the beneficial effects that maybe obtained when acquisition materials prepared by the process of the current invention are utilized in currently available commercial baby and adult diaper products. In general, it can be seen that these newly disclosed acquisition materials minimize or eliminate the trend of increasing srikethrough times with successive insults of fluid. This desired beneficial effect maybe controlled and optimized with the present invention through the control of such parameters as: the concentration of superabsorbent polymer particles applied to the web structure, the particle size distribution of the resulting superabsorbent polymer particles, the rate of swelling of the particles, the degree of swelling of the particles and the like. A further observed beneficial effect is the reduction in rewet values as shown in Table 6, below, when absorbent articles of the present invention were inserted into commercial diapers. This effect may also be controlled through the above described parameters. In addition, it is further believed that lowering the degree of neutralization of the superabsorbent particles formed on the web, thereby increasing the hydrophobicity of the particles, further enhances this effect by increasing it's tendency to be drained by the underlying wood fluff pulp/superabsorbent polymer absorbent core.

It is well known in the art that a hygienic absorbent article capable of lowering skin pH within the range of 3.0 to 5.5 is beneficial in preventing or at least reducing the incidence of diaper rash. Articles, compositions and procedures which inherently tend to lower the pH of diapered skin are also known in the art. U.S. Pat. Nos. 4,657,537, 4,382,919, 3,964,486, 3,707,148 and 3,794,034 teach the addition of various acidic pH control agents to absorbent articles or to the diapered skin environment. In those instances wherein acidic pH control agents have been incorporated into the cores of the absorbent articles, significant amounts of acids are needed to bring about the desired absorption of ammonia or lowering of skin pH. Such approaches suffer from a number of drawbacks including: decreasing the absorptive capacity of the absorbent core, safety and comfort factors associated with leaching of the materials from the article and processing problems associated with the placement and distribution of the acidic material within the absorbent core.

U.S. Pat. No. 4,657,537 discloses the preparation and use of topsheet materials containing ion exchange functionalities capable of controlling skin pH in urine soiled baby diapers, however, the ion-exchange capacities of these material are limited to the range of 0.25 to 1.0 meq./gram. Acquisition materials produced by the present invention maybe prepared to contain from 1.0 to 10 meq./gram of ion-exchanging functionalities. Examples 18 and 20 demonstrate the capability of producing acquisition materials with the ability to lower the pH both within the interior of the diaper as well as the surface.

EXAMPLES 1–5

Aqueous solutions of acrylic acid were prepared by combining 306 grams of acrylic acid, 334 grams of deionized water, 255 grams of 50% w/w sodium hydroxide, 9.1 grams of SR-9035 available from Sartomer (ethoxylated trimethylolpropane triacrylate), and 1.5 grams of 2,2'-azobis[2-(2-imidazolin-2-yl)propane]dihydrochloride. The aqueous solutions of acrylic acid were purged with nitrogen. Superabsorbent polymer particles were sieved through a 100 mesh screen and the particles passing through (having particle sizes below 150 microns) were collected. Sprayable blends were prepared by adding the collected superabsorbent polymer particles, in the amounts shown in Table 1 below, to the aqueous acrylic acid solution prepared above and stirring.

EXAMPLE 6

The sprayable blend of Example 6 was prepared in a similar manner as Examples 1–5 above, except that 158 grams of a 29% by weight aqueous solution of polyvinylpyrrolidone ("PVP") having a molecular weight of about 40,000 (PVP K 30, available from Acros Organics) was used instead of collected superabsorbent polymer particles.

The viscosity measurements reported in Table 1 below were obtained using a Brookfield Digital Viscometer Model DV-II, according to the manufacturer's directions, on 400 milliliter samples of the sprayable blends in a 600 milliliter Griffin beaker using an 02 spindle at 20 revolutions per minute. The "time" shown in Table 1, below, is the amount of time, in minutes, between adding the collected superabsorbent polymer particles and measuring the viscosity. The "weight of SAP" reported in Table 1, below, is the weight, in grams, of collected superabsorbent polymer particles, unless otherwise noted, in the sprayable blend.

TABLE 1

| Example | Weight of SAP | Viscosity (cps) | | | |
|---|---|---|---|---|---|
| | | Time = 1 | Time = 15 | Time = 30 | Time = 60 |
| 1 (comparative) | 0 | 20 | 18 | 18 | 16 |
| 2 | 15 | 20 | 22 | 22 | 22 |
| 3 | 30 | 30 | 30 | 30 | 30 |
| 4 | 45 | 46 | 54 | 52 | 52 |
| 5 | 60 | 136 | 140 | 146 | 146 |
| 6 (comparative) | 46* | 16 | 16 | 16 | 16 |

*PVP instead of collected superabsorbent polymer particles

EXAMPLES 7–13

A sprayable mixture as prepared in Example 4 or Example 1 above, as indicated in Table 2 below, was sprayed using a commercial airless paint spraying apparatus onto both sides of a 0.056 square meter piece of a polyester non-woven fabric (HDK-210 available from HDK Industries, Inc.

Rogersville, Tenn.) having a basis weight of 55 grams per square meter. The total amount of sprayable mixture retained by the fabric is reported in Table 2 below as "wet load".

The fabric was then cured either by ultraviolet radiation ("UV") or e-beam as indicated in Table 2 below. The fabrics cured by UV were passed under a 600 watt/in mercury vapor lamp, using a conveyor operating at 24 feet per minute. Each fabric was passed under the lamp twice, turned over and passed under the lamp another two times for a total exposure of 3.75 Joules UVA radiation per square centimeter on each side. Following the UV cure, the fabrics were dried in an oven for 10 minutes at 150° C. The fabrics cured by e-beam were irradiated with accelerated electrons using an electron beam apparatus for a total dose, in megarads ("Mrad"), as indicated in Table 2 below. Following the e-beam cure, the fabrics were dried in an oven for 10 minutes at 150° C. The increase in weight of the fabric is attributed to polymer and is reported as "Weight of Polymer", in grams per square meter, in Table 2, below.

The absorption under load ("AUL") is a measure of the weight of fluid retained in a material while under a load. The AUL of the fabrics prepared in Examples 7–13 as well as an untreated piece of HDK-210 was determined as follows and is reported in Table 2 below: the weight of a 5 centimeter diameter circle of the fabric was recorded; a 57 millimeter tall cylinder having an inside diameter of 5 centimeters was fitted with a metal screen approximately 2 centimeters from one end; the circle of fabric was place in the cylinder supported by the screen from below; a 711 gram weight was placed atop the fabric; the cylinder was then placed into a pan of 0.9% saline for 20 minutes such that the height of the saline was at the same level as the bottom surface of the circle of fabric, the cylinder was removed from the saline and placed on a nonabsorbent surface for one minute; the weight was removed and the weight of the fabric was recorded. The AUL, in grams per square meter, was determined using the following formula:

$$AUL = \text{Wt. 2} - \text{Wt. 1}/A$$

Wt. 2=wet web weight

Wt. 1=dry sample weight

A=area of sample in square meters ($\pi r^2$)

The centrifuge retention capacity ("CRC") is a measure of the amount of fluid retained after being centrifuged. The CRC of the fabrics prepared in Examples 7–13 as well as an untreated piece of HDK-210 was determined as follows and is reported in Table 2 below: a 5 centimeter diameter circle of the fabric was cut in half and one of the halves was placed into a teabag (6 cm×8.5 cm); the weight of the fabric prior to placing in the teabag was recorded; the teabag was sealed and placed in 0.9% saline solution for 20 minutes then centrifuged for three minutes at 1350 revolutions per minute. The weight of the centrifuged teabag was measured and the CRC, in grams per square meter, was determined using the following formula:

$$CRC = (\text{Wt. 2} - \text{Wt. 1} - \text{Blank})/A$$

Wt. 1=sample wt.

Wt. 2=teabag wt after centrifuged

Blank=wt average of two measurements of an empty teabag after centrifuging

A=area of sample in square meters [($\pi r^2$)/2] or 0.000982

The free swell capacity ("FSC") is a measure of the amount of fluid retained after soaking and hanging. This test is similar to CRC except centrifuging is omitted. The FSC of the fabrics prepared in Examples 7–13 as well as an untreated piece of HDK-210 was determined as follows and is reported in Table 2 below: a 5 centimeter diameter circle of the fabric was cut in half and one of the halves was placed into a teabag (6 cm×8.5 cm); the weight of the fabric prior to placing in the teabag was recorded; the teabag was sealed and placed in 0.9% saline solution for 20 minutes; the teabag was then removed from the saline and suspended in air for 10 minutes; The weight of the teabag was then measured and the FSC, in grams per square meter, was determined using the following formula:

$$FSC = \text{Wt. 2} - \text{Wt. 1} - \text{Blank}/A$$

Wt. 1=sample wt.

Wt. 2=weight of teabag after hanging

Blank=wt average of two measurements of an empty teabag

A=area of sample in square meters [($\pi r^2$)/2] or 0.000982

The free swell expansion volume (FSEV) is determined by measuring the height (thickness) change, in millimeters, of a compressed web material during hydration. The FSEV of the fabrics indicated in Table 3, below, were determined as follows and are reported in Table 3, below: the fabrics were compressed in a Carver Laboratory Press Model #2697 at 7000 pounds of applied load for 48 seconds with the top platen heated to 50° C.; a 5 centimeter diameter circle of the fabric was cut from the fabric and the thickness was measured before compression at approximately 4.5 millimeters and after compression at approximately 0.67 millimeters using a Fowler Ultra-digit gauge. the weight of the circle was recorded and the circle was placed in a dry sample holder; a single 20 milliliter dose of 0.9% saline was poured on top of the circle; height measurements were taken, with the help of software designed for this purpose, over a ten-minute timeframe every 1.5 seconds. The change in the height of the fabric was measured with a linear variable differential transformer (LVDT, Schaevitz MP-1000) and the data are reported in Table 3 below in milliliters (volume).

The expansion volume under load (EVUL) is determined by measuring the volume change of a sample as height (thickness) change, in millimeters, of a compressed web material during hydration while under a load. The EVUL is determined in a similar manner as the FSEV except that a 55.93 gram weight (0.5 psi load) is applied to the fabric. The EVUL values of the fabrics indicated in Table 4 were determined in this manner and the data are reported in milliliters (volume) in Table 4, below.

EXAMPLES 14 AND 15

Examples 14 and 15 were conducted in a similar manner as Examples 7–13 except that different superabsorbent polymer particles were used. The superabsorbent polymer particles used in Example 14 were lightly surface crosslinked. The superabsorbent polymer particles used in Example 15 were a mixture of the superabsorbent polymer particles used in Example 4 and the superabsorbent polymer particles used in Example 14 in an approximate weight ratio 1:2. The CRC, measured in accordance with EDANA Recommended Test Methods for Superabsorbent Materials-Polyacrylate Superabsorbent Powders, Test Method 441.1-99 and the Absorbency Against Pressure (AAP), measured in accordance with EDANA Recommended Test Methods for Superabsorbent Materials-Polyacrylate Superabsorbent Powders, Test Method 442.1-99 (using a 1319 gram cylindrical weight) of the superabsorbent polymer particles used in Examples 4, 14 and 15 are reported below:

| Superabsorbent Polymer Particles From . . . | CRC (g/g) | 0.7 psi AAP (g/g) |
|---|---|---|
| Example 4 | 43.6 | 6.2 |
| Example 14 | 22.0 | 21.9 |
| Example 15 | 31.5 | 7.8 |

EXAMPLE 16

An aqueous solution of acrylic acid was prepared by combining 368.5 grams of acrylic acid, 441.3 grams of deionized water, 90.2 grams of 50% w/w sodium hydroxide, 9.1 grams of SR-9035 available from Sartomer (ethoxylated trimethylolpropane triacrylate), and 1.5 grams of 2,2'-azobis[2-(2-imidazolin-2-yl)propane]dihydrochloride. The aqueous solution of acrylic acid was purged with nitrogen. Superabsorbent polymer particles were sieved through a 100 mesh screen and the particles passing through (having particle sizes below 150 microns) were collected. A sprayable blend was prepared by adding 23 grams of the collected superabsorbent polymer particles to the aqueous acrylic acid solution prepared above and stirring. The sprayable mixture was sprayed using a commercial airless paint spraying apparatus onto both sides of a 0.056 square meter piece of a polyester non-woven fabric (HDK-210) having a basis weight of 55 grams per square meter. The total amount of sprayable mixture retained by the fabric 17.1 grams ("wet

TABLE 2

| Example | Sprayable Mixture | Wet Load (grams) | Cure Method | Weight of Polymer (grams/sq. meter) | AUL | CRC | FSC |
|---|---|---|---|---|---|---|---|
| Untreated | | | | 0 | 1208 | 0 | 605 |
| 7 | 4 | 5.7 | UV | 43 | 2247 | 823 | 5101 |
| 8 | 4 | 8.6 | UV | 60 | 2605 | 1175 | 5669 |
| 9 | 4 | 18.9 | UV | 203 | 5208 | 3389 | 8024 |
| 10 | 4 | 33.5 | UV | 282 | 5283 | 5469 | — |
| 11 (comparative) | 1 | 33.8 | UV | 228 | 4270 | 3119 | 8913 |
| 12 | 4 | 19.3 | UV followed by E-beam; 8 Mrad | 210 | 4193 | 2436 | 7067 |
| 13 | 4 | 19.3 | E-beam; 16 Mrad | 233 | 4348 | 3734 | — |
| 14* | 4* | 19.7 | UV | 110 | 3848 | 6865 | 2230 |
| 15** | 4** | 19.3 | UV | 125 | 3512 | 8299 | 2415 |

*The superabsorbent polymer particles used were lightly surface crosslinked.
**The superabsorbent polymer particles used were a mixture of the superabsorbent polymer particles used in Example 4 and the superabsorbent polymer particles used in Example 14 in an approximate weight ratio 1:2.

The web prepared in example 11, compared to the webs prepared in examples 7–10, was much more brittle and less flexible. Examination of these webs under a microscope also showed that the webs prepared in examples 7–10 exhibited more uniform particle size distribution and had fewer regions of film formation (as opposed to discrete particle adherence) on the surface of the web and in the interstitial pore volume of the web.

TABLE 3

| EXAMPLE | Weight of Polymer (grams/sq. meter) | FSEV (milliliters) | | | | | | |
|---|---|---|---|---|---|---|---|---|
| | | 5 sec. | 10 sec | 30 sec | 60 sec | 120 sec | 300 sec | 600 sec |
| Untreated | 0 | 0.3 | 0.3 | 0.3 | 0.3 | 0.3 | 0.3 | 0.3 |
| Example 7 | 43 | 1.8 | 2.5 | 3.4 | 3.7 | 3.9 | 3.9 | 3.9 |
| Example 8 | 60 | 1.9 | 2.9 | 4.1 | 4.8 | 5.3 | 5.6 | 5.6 |
| Example 9 | 203 | 1.4 | 2.2 | 4.3 | 5.9 | 7.3 | 8.5 | 9.0 |
| Example 10 | 282 | 1.7 | 2.8 | 5.3 | 7.1 | 8.6 | 9.8 | 10.2 |

TABLE 4

| EXAMPLE | Weight of Polymer (grams/sq. meter) | EVUL (milliliters) | | | | | | |
|---|---|---|---|---|---|---|---|---|
| | | 5 sec. | 10 sec | 30 sec | 60 sec | 120 sec | 300 sec | 600 sec |
| Untreated | 0 | 0.3 | 0.3 | 0.3 | 0.3 | 0.3 | 0.3 | 0.3 |
| Example 7 | 43 | 0.6 | 0.9 | 1.2 | 1.4 | 1.4 | 1.5 | 1.5 |
| Example 8 | 60 | 0.6 | 0.8 | 1.3 | 1.5 | 1.7 | 1.8 | 1.8 |
| Example 9 | 203 | 0.8 | 1.0 | 1.6 | 2.1 | 2.5 | 2.9 | 3.0 |
| Example 10 | 282 | 0.8 | 0.9 | 1.5 | 2.2 | 3.0 | 3.6 | 3.9 | load"). The fabric was then cured by ultraviolet radiation ("UV") by passing the fabric under a 600 watt/in mercury vapor lamp, using a conveyor operating at 24 feet per minute. The fabric was passed under the lamp twice, turned over and passed under the lamp another two times for a total exposure of 3.75 Joules of UVA per square centimeter on each side. Following the UV cure, the fabric was dried in an oven for 10 minutes at 150° C. The Weight of Polymer in the resulting fabric was 82.9 grams per square meter.

EXAMPLES 17–20

The following two commercial diapers were used to prepare the experimental samples described below:

Diaper A:
  medium, adult brief
  Core: homogeneous wood fluff/superabsorbent polymer pad
  Weight ratio of wood fluff to superabsorbent polymer in core: 38.8 grams: 7.2 grams
  Secondary chemically treated mechanical pulp ("CTMP") core, 23.0 grams
  Random, pinpointed bonded top sheet
  Density of core: 0.08 grams per cubic centimeter
  Density of secondary CTMP core: 0.09 grams per cubic centimeter Diaper B:
  medium, baby
  Core: homogeneous wood fluff/superabsorbent polymer pad
  Weight ratio of wood fluff to superabsorbent polymer in core: 19.7 grams: 10.3 grams
  Polypropylene, point bonded top sheet
  Density of core: 0.15 grams per cubic centimeter Experimental diapers were prepared by stretching out Diaper A and Diaper B and taping them to a laboratory bench top. The experimental fabric, as indicated in Table 5 below, was compressed under a 7000 pound load for 48 seconds using a Carver laboratory press with the top platen heated to 50° C. The thickness of the fabric following compression was 0.67 millimeters. An Exacto razor knife was used to carefully cut along the edges of the top sheet to expose the diaper core. In the case of Diaper A, the secondary CTMP core was removed and replaced with the compressed experimental fabric as indicated in Table 5 below. In the case of Diaper B, the high loft non-woven (basis weight of 45 grams per square meter) was removed and replaced with the compressed experimental fabric as indicated in Table 5 below.

TABLE 5

|  | Commercial Diaper | Fabric from |
| --- | --- | --- |
| Example 17 | Diaper A | Example 9 |
| Example 18 | Diaper A | Example 16 |
| Example 19 | Diaper B | Example 9 |
| Example 20 | Diaper B | Example 16 |

The commercial and experimental diapers were evaluated with a rewet test which measures the amount of unabsorbed liquid left on the surface of a wetted diaper. The rewet values reported in Table 6 below, were determined by taping the diaper to a Plexiglas® board or to the counter top, insulting the center of the diaper with 0.9% saline using a dosing ring (5 centimeter inside diameter with 2.5 centimeter height). Diaper A and examples 15 and 16 were insulted with 100 milliliters of the saline. Diaper B and examples 17 and 18 were insulted with 80 milliliters of the saline. The amount of time needed for the liquid to be absorbed from the surface of the diaper was recorded as the strike through time. After 20 minutes a stack of Whatman #3, 9.0 cm diameter filter paper (W1) was weighed and placed on top of the insulted area. A 3620-gram weight was placed on the filter paper for two minutes. The stack of filter paper was reweighed and the weight recorded (W2). This procedure was repeated two more times, recording the filter paper weight change and the strike through times. The pH of the top sheet, the transfer layer (if any) and the core were measured after the experiment was complete using a Ross Flat Surface Epoxy Combination pH Model #8235 electrode; the data are reported in Table 7, below.

The rewet values were calculated as follows:

W2−W1=rewet value (grams)

The rewet and strikethrough data reported in Table 6, below, are the average values of the results conducted on three separate diapers.

TABLE 6

|  | REWET (grams) | | | STRIKETHROUGH TIME (seconds) | | |
| --- | --- | --- | --- | --- | --- | --- |
| EXAMPLE | 1st DOSE | 2nd DOSE | 3rd DOSE | 1st DOSE | 2nd DOSE | 3rd DOSE |
| Commercial Diaper A | 0.8 | 14 | 29 | 15.5 | 19.7 | 25.8 |
| Example 17 | 0.3 | 7.8 | 25.7 | 4.7 | 7.4 | 9.6 |
| Example 18 | 1.1 | 8.1 | 18.4 | 4.4 | 4.8 | 4.9 |
| Commercial Diaper B | 0.08 | 0.15 | 8.0 | 7.6 | 7.6 | 16.3 |
| Example 19 | 0.13 | 0.34 | 3.1 | 4.3 | 5.4 | 6.8 |
| Example 20 | 0.56 | 0.65 | 0.78 | 3.3 | 4.0 | 4.3 |

TABLE 7 pH MEASUREMENTS OF DIAPER SURFACES

| EXAMPLE | TOPSHEET | ACQUISITION LAYER | FLUFF/SAP CORE |
| --- | --- | --- | --- |
| Commercial Diaper A | 5.3 | 5.4 | 5.8 |
| Example 17 | 5.3 | 5.6 | 5.9 |
| Example 18 | 4.7 | 4.4 | 5.1 |

TABLE 7-continued pH MEASUREMENTS OF DIAPER SURFACES

| EXAMPLE | TOPSHEET | ACQUISITION LAYER | FLUFF/SAP CORE |
|---|---|---|---|
| Commercial Diaper B | 5.3 | 5.4 | 5.8 |
| Example 19 | 5.3 | 5.6 | 5.9 |
| Example 20 | 4.5 | 4.5 | 5.1 |

We claim:

1. A process comprising:
   forming a sprayable blend comprising
      one or more superabsorbent forming monomers
      superabsorbent polymer particles
      water, and
      one or more initiators;
   spraying said sprayable blend onto a fibrous web; and
   subjecting said fibrous web to conditions under which the superabsorbent forming monomer will polymerize.

2. The process of claim 1 wherein the sprayable blend further comprises a crosslinking compound.

3. An absorbent article prepared by the process of claim 1 or claim 2.

4. A disposable hygiene article comprising a back sheet, an absorbent core and an absorbent article as claimed in claim 3.

* * * * *